(12) United States Patent
Aikens et al.

(10) Patent No.: US 8,543,557 B2
(45) Date of Patent: Sep. 24, 2013

(54) EVOLUTION OF LIBRARY DATA SETS

(75) Inventors: David M. Aikens, Pleasanton, CA (US);
Youxian Wen, Livermore, CA (US);
Walter Lee Smith, Danville, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 1402 days.

(21) Appl. No.: 11/096,845

(22) Filed: Apr. 1, 2005

(65) Prior Publication Data
US 2005/0182592 A1    Aug. 18, 2005

Related U.S. Application Data

(63) Continuation of application No. 10/145,848, filed on May 14, 2002, now Pat. No. 6,898,596.

(60) Provisional application No. 60/346,252, filed on Oct. 23, 2001, provisional application No. 60/351,494, filed on Jan. 24, 2002.

(51) Int. Cl.
*G06F 7/00*       (2006.01)

(52) U.S. Cl.
USPC .................................................. 707/700

(58) Field of Classification Search
USPC ............... 707/104.1, 10, 100, 3, 6, 999.101, 707/999.102, 700
See application file for complete search history.

(56) References Cited

U.S. PATENT DOCUMENTS

| | | | |
|---|---|---|---|
| 3,704,522 A * | 12/1972 | Blubaugh et al. | 33/286 |
| 4,365,303 A * | 12/1982 | Hannah et al. | 702/28 |
| 5,239,366 A * | 8/1993 | Kittell et al. | 356/609 |
| 5,607,800 A | 3/1997 | Ziger | 430/8 |
| 5,739,909 A * | 4/1998 | Blayo et al. | 356/369 |
| 5,789,124 A * | 8/1998 | Todd | 430/30 |
| 5,864,633 A | 1/1999 | Opsal et al. | 382/141 |
| 5,867,276 A | 2/1999 | McNeil et al. | 356/445 |

(Continued)

FOREIGN PATENT DOCUMENTS

| | | |
|---|---|---|
| WO | WO 99/45340 | 9/1999 |
| WO | WO 01/69403 A1 | 9/2001 |

(Continued)

OTHER PUBLICATIONS

C.J. Raymond et al., "Scatterometry for the measurement of metal features," In *Metrology, Inspection, and Process Control for Microlithography XIV*, Neal T. Sullivan, Editor, Proceedings of SPIE, vol. 3998, 2000, pp. 135-146.

*Primary Examiner* — Eliyah S Harper
(74) *Attorney, Agent, or Firm* — Morrison & Foerster LLP

(57) ABSTRACT

An optical metrology includes a library, a metrology tool and a library evolution tool. The library is generated to include a series of predicted measurements. Each predicted measurement is intended to match the measurements that a metrology device would record when analyzing a corresponding physical structure. The metrology tool compares its empirical measurements to the predicted measurements in the library. If a match is found, the metrology tool extracts a description of the corresponding physical structure from the library. The library evolution tool operates to improve the efficiency of the library. To make these improvements, the library evolution tool statistically analyzes the usage pattern of the library. Based on this analysis, the library evolution tool increases the resolution of commonly used portions of the library. The library evolution tool may also optionally reduce the resolution of less used portions of the library.

4 Claims, 3 Drawing Sheets

(56) References Cited

U.S. PATENT DOCUMENTS

| | | | |
|---|---|---|---|
| 5,917,594 A * | 6/1999 | Norton | 356/327 |
| 5,963,329 A | 10/1999 | Conrad et al. | 356/613 |
| 6,032,151 A * | 2/2000 | Arnold et al. | 1/1 |
| 6,115,718 A * | 9/2000 | Huberman et al. | 1/1 |
| 6,141,657 A | 10/2000 | Rothberg et al. | 707/6 |
| 6,195,652 B1 * | 2/2001 | Fish | 1/1 |
| 6,281,027 B1 * | 8/2001 | Wei et al. | 438/14 |
| 6,309,900 B1 * | 10/2001 | Maury et al. | 438/16 |
| 6,323,946 B1 * | 11/2001 | Norton | 356/327 |
| 6,334,122 B1 * | 12/2001 | Brown | 1/1 |
| 6,393,038 B1 * | 5/2002 | Raymond et al. | 372/22 |
| 6,397,225 B1 * | 5/2002 | Brown et al. | 1/1 |
| 6,480,854 B1 * | 11/2002 | Gross et al. | 1/1 |
| 6,643,557 B1 * | 11/2003 | Miller et al. | 700/110 |
| 6,757,645 B2 * | 6/2004 | Chang et al. | 703/13 |
| 6,768,967 B2 | 7/2004 | Johnson et al. | 702/179 |
| 7,099,005 B1 * | 8/2006 | Fabrikant et al. | 356/369 |
| 2002/0018217 A1 | 2/2002 | Weber-Grabau et al. | 356/601 |
| 2002/0033954 A1 | 3/2002 | Niu et al. | 356/601 |
| 2002/0035455 A1 * | 3/2002 | Niu et al. | 703/4 |

FOREIGN PATENT DOCUMENTS

| | | |
|---|---|---|
| WO | WO 01/75425 A2 | 10/2001 |
| WO | WO 01/97280 A2 | 12/2001 |
| WO | WO 02/27288 A1 | 4/2002 |

* cited by examiner

Fig. 10
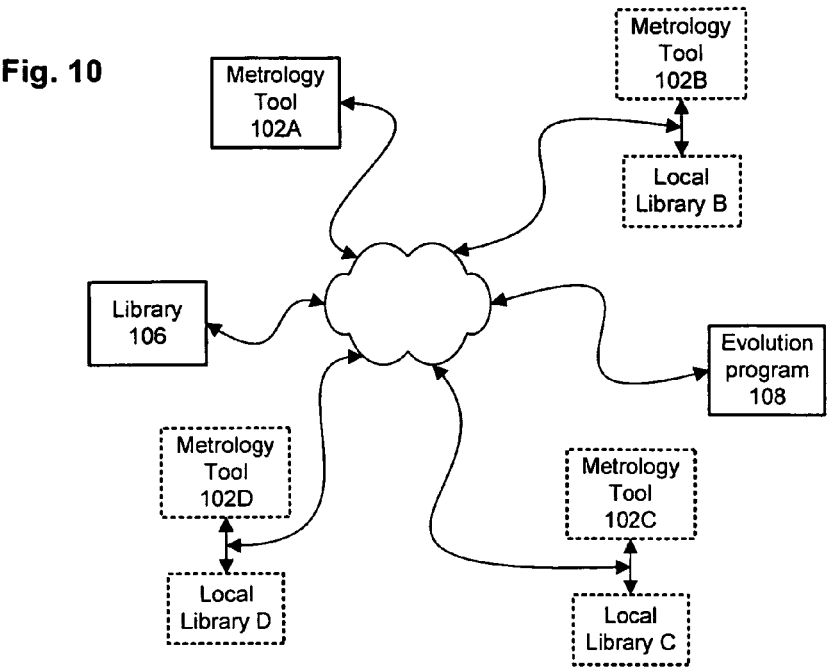
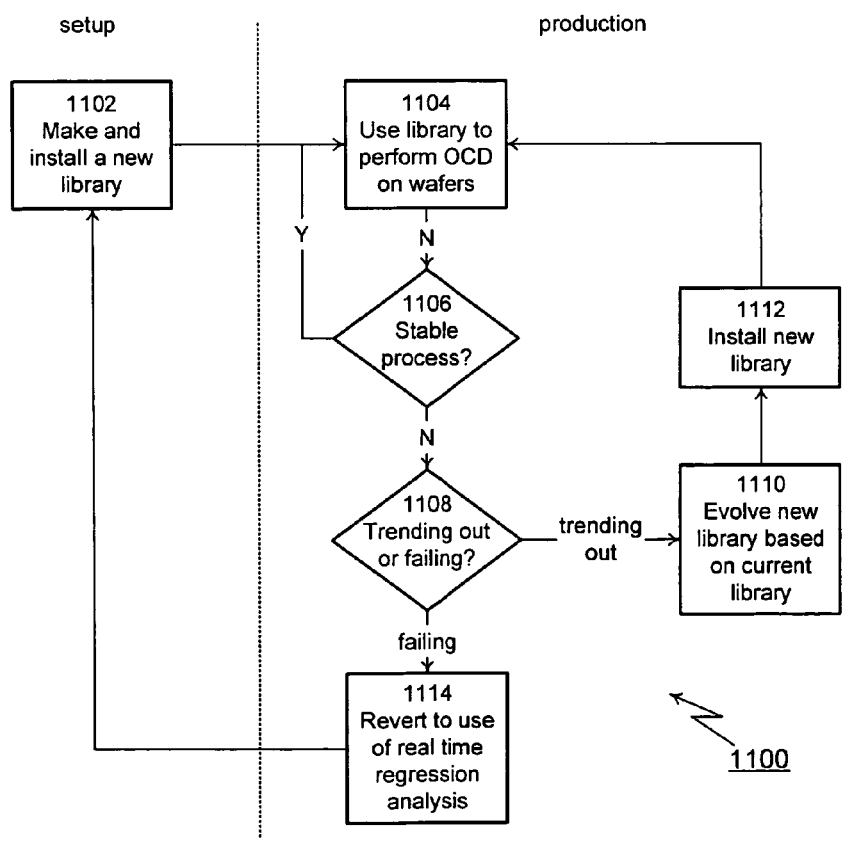
Fig. 11

EVOLUTION OF LIBRARY DATA SETS

CLAIM OF PRIORITY

The present application is a continuation of U.S. patent application Ser. No. 10/145,848, entitled "EVOLUTION OF LIBRARY DATA SETS," filed May 14, 2002 now U.S. Pat. No. 6,898,596, which claims priority to U.S. Provisional Patent Application Ser. No. 60/346,252, filed Oct. 23, 2001 and Ser. No. 60/351,494, filed Jan. 24, 2002, all of which are hereby incorporated herein by reference.

TECHNICAL FIELD OF THE INVENTION

The subject invention relates to the use of data sets or libraries to facilitate the analysis of experimental samples. In particular, an approach is disclosed that improves the speed, versatility and efficiency of libraries used for this purpose.

BACKGROUND

Over the past several years, there has been considerable interest in using optical scatterometry (i.e., optical diffraction) to perform critical dimension (CD) measurements of the lines and structures included in integrated circuits. Optical scatterometry has been used to analyze periodic two-dimensional structures (e.g., line gratings) as well as three-dimensional structures (e.g., patterns of vias or mesas). Scatterometry is also used to perform overlay registration measurements. Overlay measurements attempt to measure the degree of alignment between successive lithographic mask layers.

Various optical techniques have been used to perform optical scatterometry. These techniques include broadband scatterometry (U.S. Pat. Nos. 5,607,800; 5,867,276 and 5,963,329), spectral ellipsometry (U.S. Pat. No. 5,739,909) as well as spectral and single-wavelength beam profile reflectance and beam profile ellipsometry (co-pending application Ser. No. 09/818,703 filed Mar. 27, 2001). In addition it may be possible to employ single-wavelength laser BPR or BPE to obtain CD measurements on isolated lines or isolated vias and mesas.

Most scatterometry systems use a modeling approach to transform scatterometry signals into critical dimension measurements. For this type of approach, a theoretical model is defined for each physical structure that will be analyzed. The theoretical model predicts the empirical measurements (scatterometry signals) that scatterometry systems would record for the structure. A rigorous coupled wave theory can be used for this calculation. The theoretical results of this calculation are then compared to the measured data (actually, the normalized data). To the extent the results do not match, the theoretical model is modified and the theoretical data is calculated once again and compared to the empirical measurements. This process is repeated iteratively until the correspondence between the calculated theoretical data and the empirical measurements reaches an acceptable level of fitness. At this point, the characteristics of the theoretical model and the physical structure should be very similar.

The calculations discussed above are relatively complex even for simple models. As the models become more complex (particularly as the profiles of the walls of the features become more complex) the calculations become exceedingly long and complex. Even with high-speed processors, the art has not developed a suitable approach for analyzing more complex structures to a highly detailed level on a real time basis. Analysis on a real time basis is very desirable so that manufacturers can immediately determine when a process is not operating correctly. The need is becoming more acute as the industry moves towards integrated metrology solutions wherein the metrology hardware is integrated directly with the process hardware.

One approach that allows a manufacturer to characterize features in real time is to create "libraries" of predicted measurements. This type of approach is discussed in PCT application WO 99/45340, published Sep. 10, 1999 as well as the references cited therein. In this approach, the theoretical model is parameterized to allow the characteristics of the physical structure to be varied. The parameters are varied over a predetermined range and the theoretical result for each variation to the physical structure is calculated to define a library of solutions. When the empirical measurements are obtained, the library is searched to find the best fit.

In general, libraries have proven to be an effective method for quickly analyzing samples. Unfortunately, libraries have also proven to have their own disadvantages. One disadvantage results from the fact that libraries must be generated in a reasonable amount of time and must occupy a reasonable amount of space. This means that libraries must have limited range (i.e., the library is limited to a portion of the total solution space). Libraries must also have limited resolution (i.e., there must be some granularity between solutions). These limitations become problematic when test data doesn't closely match the range and resolution of the library being used. If a library has inadequate range, for example, test data may not match any of the library's stored solutions. This same result can occur when a library has adequate range, but the range is incorrectly centered in the spectrum of solutions. Libraries may also have inadequate resolution causing test data to fall between stored solutions. In other cases, libraries may have excessive range or resolution wasting both time and space.

One approach for dealing with this problem is to use the library values as a starting point for the solution and then determine parameters using interpolation or estimation procedures. U.S. Pat. No. 5,867,276 describes a system of training a library to permit linear estimations of solutions. Another form of interpolation can be found in U.S. Patent Application 2002/0038196, published Mar. 28, 2002. PCT WO 02/27288, published Apr. 4, 2002 suggests using a coarse library and a real time regression approach to improve results. The latter documents are incorporated by reference.

Even using the above approaches, the initial libraries in working optical metrology systems are seldom optimal for either range or resolution. This follows because optimal values for range and resolution are difficult to predict as libraries are being built. Inevitable errors in these predictions mean that libraries are never entirely efficient at analyzing test results. Errors of this type often compound, as libraries are used and operational parameters change or drift. In these cases, libraries become increasingly out of sync with their optical metrology systems and increasingly inefficient at analyzing test results. A more ideal solution would be to develop a system that adapted libraries to the actual test results generated by optical metrology systems.

BRIEF SUMMARY

An aspect of the present invention provides a library evolution method for use with optical metrology systems. Systems of this type use a library for each physical structure that will be analyzed. The library for each structure is based on a corresponding parametric model. The parametric model predicts the empirical measurements that a metrology system would record for the structure. The parameters allow the model to be varied or perturbed, to produce a series of predicted measurement sets. Each library contains a series of predicted measurements sets, each set corresponding to a particular set of model parameters.

The underlying parametric model may be used to predict empirical measurements that are associated with a wide range of attributes within the physical structure being modeled. In semiconductor wafers, two-dimensional structures (e.g., line gratings) as well as three-dimensional structures (e.g., patterns of vias or mesas) are often modeled. The structures may be modeled as parts of a surface layer or as parts of subsurface layers. Models may also account for layer properties, such as transparency, thickness and type for both surface and subsurface layers. In some cases, alignment between different layers may also be modeled.

As the optical metrology system operates, its empirical measurements are compared to the predicted measurement sets stored in the library. If a match is found, the parameters used to generate the matching set of predicted measurements are assumed to describe the physical structure being analyzed. In the best case, the process of library searching results in matches most, if not all of the time. This results when the library has been constructed to have the correct range and resolution. Range, in this context, means that the predicted measurement sets in the library span the range of empirical measurements that are encountered empirically. Resolution means that the granularity of predicted measurement sets within the library is fine enough that close matches may be found for the empirical measurements that are encountered empirically. In real-world systems, where computational and storage resources are limited, range and resolution of a given library must be limited.

The library evolution method dynamically optimizes the range and resolution of a library to correspond to the empirical measurements that are encountered empirically. Optimization may be applied to a library as initially created or to a previously optimized library. To optimize a library, the evolution method monitors the library's use. As the library is used a usage pattern is generated. The usage pattern identifies the portions of the library that are heavily used along with the portions that are less used or unused.

A library evolution program reorganizes the library based on the usage pattern. The library program generates new predicted measurement sets in portions of the library where additional resolution or range would be beneficial. Optionally, the library evolution program may also delete predicted measurement sets to reduce unneeded range or resolution. The overall effect is to transform the library to have range and resolution that matches the actual use of the library. This process may be performed continuously, in parallel with the use of the library, or performed as an offline process at periodic intervals.

It should also be appreciated that the library evolution method may be applied to a wide range of systems and is not limited to use within optical metrology systems.

BRIEF DESCRIPTION OF THE DRAWINGS

FIG. 10 is a block diagram showing a representative networked deployment of the present invention.

FIG. 11 is a functional chart showing fault tolerant operation of the present invention.

DETAILED DESCRIPTION

Figure 1:
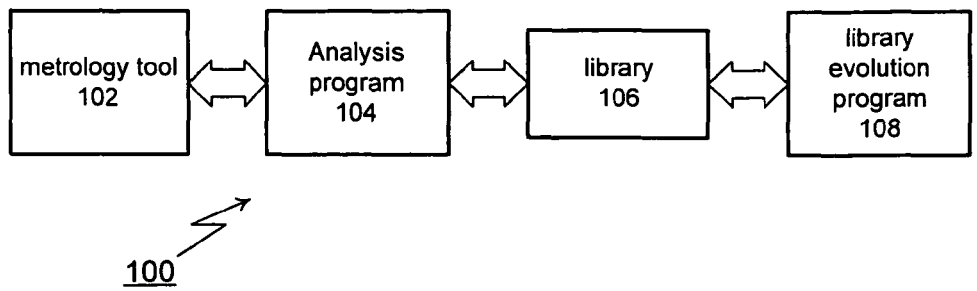
FIG. 1 is a block diagram of the software components used by an optical metrology system using the library evolution method of the present invention.

An aspect of the present invention provides a method for improving the speed, accuracy and versatility of programs that use libraries as part of their problem solving strategies. To describe this method, FIG. 1 shows a representative use of the present invention as part of an optical metrology system 100. As previously described, systems of this type are typically used to inspect semiconductor wafers by analyzing periodic two-dimensional structures (e.g., line gratings) as well as three-dimensional structures (e.g., patterns of vias or mesas). Overlay registration measurements may also be performed to quantify the degree of alignment between successive lithographic mask layers.

As shown in FIG. 1, optical metrology system 100 includes a metrology tool 102, an analysis program 104, an evolution program 108 and a library 106. Metrology tool 102 is representative of the wide range of tools of this nature. For this particular example, metrology tool 102 may be assumed to be one of systems available from Therma-Wave Inc. Analysis program 104 controls the operation of metrology tool 102 and interprets its empirical measurements.

Library 106 is created by modeling one or more physical structures. For the modeling process, each physical structure is described using a corresponding parametric model. The parametric model predicts the empirical measurements that metrology tool 102 would record for the corresponding physical structure. The parameters allow the model to be varied or perturbed, to create a series of similar physical structures and a corresponding series of predicted measurement sets. Library 106 contains a series of predicted measurements sets generated in this fashion. Library 106 also contains the parameters used to generate the predicted measurements sets. Within library 106, each set of predicted measurements is associated with the parameters used during its generation.

The underlying parametric model may be used to predict empirical measurements that are associated with a wide range of attributes within the physical structure being modeled. In semiconductor wafers, two-dimensional structures (e.g., line gratings) as well as three-dimensional structures (e.g., patterns of vias or mesas) are often modeled. The structures may be modeled as parts of a surface layer or as parts of subsurface layers. Models may also account for layer properties, such as transparency, thickness and type for both surface and subsurface layers. In some cases, alignment between different layers may also be modeled.

After metrology tool 102 has inspected a sample, analysis program 104 compares the resulting empirical measurements to the predicted measurement sets stored in library 106. If a match is found, the parameters used to generate the matching set of predicted measurements are assumed to describe the physical structure being analyzed. In the best case, the process of searching library 106 results in matches most, if not all of the time. This results when library 106 has been constructed to have an optimal range and resolution. Range, in this context, means that the predicted measurement sets in library 106 span the range of empirical measurements that are encountered empirically. Resolution means that the granularity of predicted measurement sets within library 106 is fine enough that close matches may be found for the empirical measurements that are encountered empirically. In real-world systems, where computational and storage resources are limited, both the range and resolution of library 106 must be limited.

Evolution program 108 dynamically optimizes the range and resolution of library 106 to correspond to the empirical measurements that are encountered empirically by optical metrology tool 102. Optimization may be applied to library 106 as initially created or at any time thereafter. To perform this optimization, analysis program 104 monitors the use of library 106. As library 106 is used a usage pattern is generated. The usage pattern identifies the portions of the library 106 that are heavily used along with the portions that are less used or unused. Based on the usage pattern, evolution program 108 generates new predicted measurement sets in portions of library 106 where additional resolution or range would be beneficial. Optionally, evolution program 108 may also delete predicted measurement sets to reduce unneeded range or resolution within less used portions of library 106. The overall effect is to transform library 106 to have range and resolution that match the empirical measurements actually encountered by optical metrology tool 102.

Figure 2:
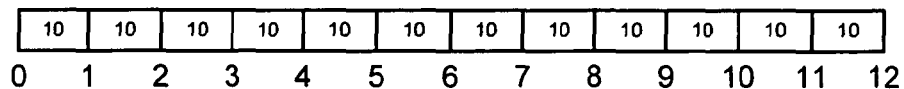
FIG. 2 is a block diagram of a simplified library shown as a target for the library evolution method of the present invention.

To better describe the evolution process, FIG. 2 shows a simplified version of library 106. In FIG. 2, library 106 includes a series of one hundred twenty (120) predicted measurements, evenly distributed within the range of zero to twelve. The resolution within library 106 is ten predicted measurement sets per unit of range.

Figure 3:
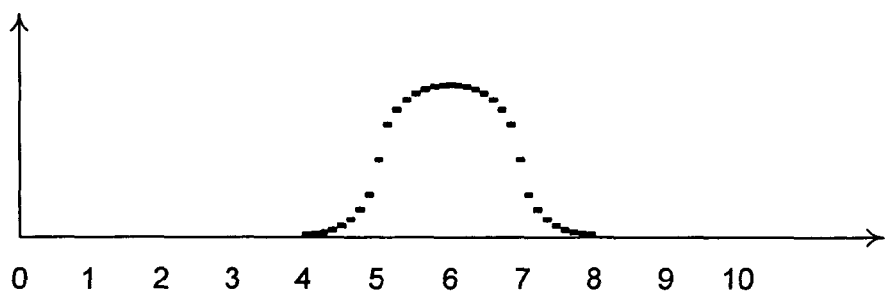
FIG. 3 is an example of a usage pattern that might correspond to the library of FIG. 2.

FIG. 3 shows a hypothetical usage pattern for library 106 of FIG. 2. The usage pattern is a statistical record of the searches performed on library 106. This includes both successful and unsuccessful searches and includes searches that fall within or outside of the current range of library 106. As shown in the example usage pattern of FIG. 3, two-thirds of library 106 is unused. The remaining portions of library 106 are more heavily used with the greatest used restricted to a mere one-sixth of library 106. In general, it should be appreciated that the usage pattern generated for library 106 includes both successful and unsuccessful searches both inside and outside of the range of library 106.

Figure 4:
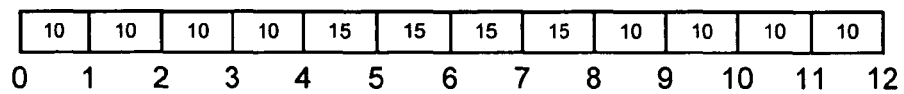
FIG. 4 is a block diagram of a library data set evolved from the library data set of FIG. 2 after the addition of new predicted measurement sets based on the usage pattern of FIG. 3.

To make library 106 more closely match the usage pattern of FIG. 3, evolution program 108 generates new predicted measurement sets within the most used portions of library 106. This is shown in FIG. 4 where evolution program 108 has generated twenty new predicted measurement sets. As a result, the most commonly used portion of library 106 now has the greatest number of predicted measurement sets and the highest resolution.

Figure 5:
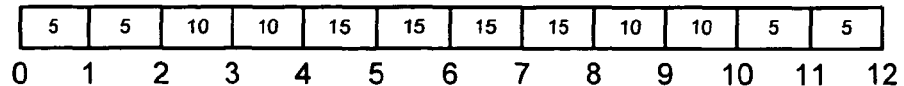
FIG. 5 is a block diagram of a library data set evolved from the library data set of FIG. 4 after the removal of predicted measurement sets based on the usage pattern of FIG. 3.

Optionally, evolution program 108 may also prune the regions of library 106 that are least used. This is shown in FIG. 5 where evolution program 108 has removed twenty of the predicted measurement sets within the least used regions of library 106. As a result of the enhancement and pruning operations, the most commonly used portion of library 106 now has the greatest number of predicted measurements. The least used portions of library 106 have the smallest number of predicted measurements. The overall result is that library 106 includes three distinct levels of resolution. The outer regions, which receive the least use, contain the smallest number of predicted measurements. An intermediate region includes more predicted measurements and the inner, most-heavily used region includes the most predicted measurements. This closely approximates the pattern of use shown in FIG. 3. Of course, an even more aggressive reorganization could have been performed using the same basic method.

Figure 6:
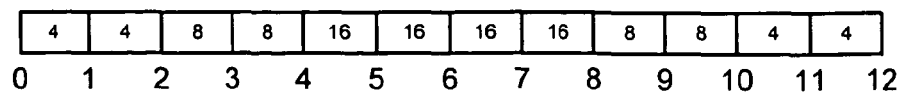
FIG. 6 is a block diagram of a library data set evolved from the library data set of FIG. 2 after a second possible enhancement based on the usage pattern of FIG. 3.

Several methods exist for identifying portions of library 106 for pruning or enhancement. One method is to statistically evaluate the usage of library 106. The statistical evaluation identifies mean and standard deviations for the usage pattern. Evolution program 108 then repopulates library 106 so that library density increases in regions closest to the mean value and decreases at successively greater standard deviations from the mean. FIG. 6 can be used to illustrate this type of reorganization if it is assumed that the mean value is six and the standard deviation is two. Within that figure, the region within one standard deviation (i.e., four through eight) has a total of sixty-four predicted measurement sets. The region within two standard deviations (i.e., two through four and eight through ten) has approximately half as many predicted measurements (in this case, thirty-two). The region within three standard deviations (i.e., zero through two and ten through twelve) has approximately half again as many predicted measurements (in this case, sixteen). The samples are therefore, distributed using a power of two distribution where each more distant region (standard deviation) has half of the sample population as the preceding region.

The standard deviation based reorganization is beneficial because it automatically adapts to perform library annealing and diffusing (i.e., increases or decreases in library density to accommodate different usage patterns) as well as library centering (i.e., shifts in the range covered by the library).

Figure 7:
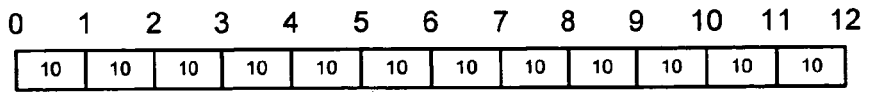
FIG. 7 is a block diagram showing use of a vector to record the usage of the library of FIG. 2.
Figure 8:
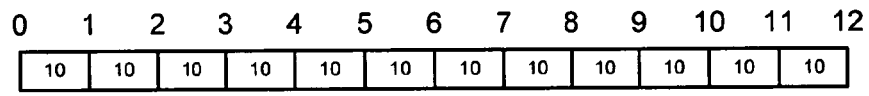
FIG. 8 is a block diagram showing the vector of FIG. 7 after use of the library for a statistically significant time period.

Another approach is to configure library 106 to maintain usage counts for sub-ranges within library 106. The sub-ranges can be created with any desired granularity. FIG. 7 shows a representative implementation where each sub-range covers one range unit (e.g., 0 to 1, 1 to 2, 2 to 3 and so on). A vector of usage counters tracks the number of searches within a particular sub-range. As shown in FIG. 7, the usage counts are initially set to zero. Each counter is incremented each time a search is performed within its associated sub-range. FIG. 8 continues this example to a point in time where the incrementing process has been repeated a statistically significant number of times. As shown in FIG. 8, the usage counts that correspond to the region between two and four are highest. The usage counts for the regions one to two and four to five are next highest.

The usage counts for the regions zero to one and five to six are next highest. The remaining usage counts are zero. As indicated by the vector of usage counts, library 106 (for this example) is suboptimal both for range and resolution. Only a small portion of library 106 is used. In addition, it may be assumed that searches are performed beyond the range of library 106.

Figure 9:
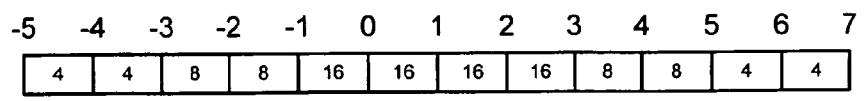
FIG. 9 is a block diagram showing reorganization of the library of FIG. 2 based on the usage vector of FIG. 8.

FIG. 9 illustrates redistribution of library 106 by evolution program 108 based on the usage vector of FIG. 8. As shown in FIG. 9, evolution program 108 has selectively pruned and augmented library 106 to match the usage vector. The most heavily used portions of library 106 now have the highest resolution. The least used regions have the lowest resolution. The library has been effectively shifted to center its range around its most searched sub-ranges. The usage vector of library 106 has also been reinitialized so all usage counts are zero. The process of library use (with the usage recording vector a new usage pattern) followed by analysis and optimization by evolution program 108 can be repeated any number of times.

The usage vector approach is beneficial because it automatically adapts to perform library annealing and diffusing (i.e., increases or decreases in library density to accommodate different usage patterns) as well as library centering (i.e., shifts in the range covered by the library). The usage vector approach also adapts to arbitrary usage patterns that might be difficult to accommodate using other approaches.

It should be noted that usage is not the only factor that is relevant when evolving library 106. For example, it could be the case that different predicted measurements within library 106 have different associated values. This could occur when several different methods are used to generate predicted measurements with some of the methods being more costly or time consuming that other methods. In this sort of case, evolution program can be configured to account for additional factors as part of the pruning and enhancement process. Entries within the usage vector could be marked with a special "do not delete" value where certain predicted measurements should be maintained indefinitely. The usage vector can also be augmented to include a value entry for each predicted measurement. Each value entry would be initialized to include the value of the corresponding predicted measurement allowing evolution program 106 to account for value when choosing which predicted measurements to prune.

It should be noted that the steps of evolving library 106 may include genetic algorithms to improve or increase the population of predicted measurements. The use of genetic algorithms in optical metrology is described in U.S. Pat. No. 5,864,633 as well as in PCT WO 01/75425, both incorporated herein by reference.

Software Architecture

The evolution method may be implemented using a wide range of different software architectures. For the architecture shown in FIG. 1, evolution program 108 and metrology tool 102 coexist on a single system (or cluster). Evolution program 108 works as a parallel background process to improve library 106 while metrology tool 102 is being used to analyze empirical measurements. For a second architecture, shown in FIG. 10 metrology tool 102, evolution program 108 and library 106 operate in a networked environment. Within this environment, metrology tool 102, evolution program 108 and library 106 are hosted on one or more separate computer systems. Operation of metrology tool 102 remotely from evolution program 108 increases the throughput of both programs since they no longer compete for the same system resources.

Remote operation has other advantages as well. As shown in FIG. 10, evolution program 108 and library 106 may be shared between metrology tool 102 and one or more different metrology tools (shown as metrology tools 102*b*, 102*c* and 102*d*). The networking of these various components allows a single library 106 and a single evolution program 108 to service a range of different tools.

Metrology tools 102 may also be configured to have local libraries. These local libraries are maintained by evolution program 108 in the same fashion as library 106. The local libraries may be configured for exclusive use by their associated metrology tool 102 or for shared use by one or more remote metrology tools 102 (e.g, the local library of metrology tool 102*b* can be shared between metrology tools 102*a*, 102*b* and 102*c*). Metrology tools 102 may use a selection process to select a local library for use. This allows metrology tools 102 to choose an alternate library and continue operation in cases where a currently used library becomes ineffective.

The local libraries may be configured to operate in place of or to supplement library 106. In cases where the local libraries supplement library 106, evolution program 108 may populate each local library to selectively enhance the areas of library 106 that are most used by the corresponding metrology tool 10. In these cases, each local library is evolved to act as a cache for the predicted results most used by the associated metrology tool 102. Metrology tools 102 would access library 106 only for less used predicted results.

Fault-Tolerant Library Evolution

In most applications, metrology tool 102, evolution program 108 and library 106 will be used as part of a production process. The importance of maintaining production on a continuous basis is often paramount. As a result, it is important that evolution program 108 operate in fault tolerant manner. A method 1100 for fault tolerant operation is shown in FIG. 11. For this method, library 106 is initially generated using the previously described modeling process (see step 1102). Once generated, library 106 is installed for use.

As library 106 is used, its performance is monitored (see steps 1104 and 1106). Typically, this is done by a monitoring process or thread and may be done on a periodic or continuous basis. As long as the performance of library 106 meets preset criteria, it will continue to be used.

The alternative (see step 1108) occurs when the library performance has become unacceptable. In this case, a determination is made as to whether the use of library 106 is trending out. In this context, trending out means that the use of library 106 has changed in some way that is addressable by evolution program 108. As discussed previously, this would include cases where library 106 is fixable by changes in library density in a given area (library annealing and diffusing) or changed in data ranges (library centering). If the use of library 106 is trending out, modification of library 106 is undertaken by evolution program 108 (step 1110). When complete, the modified library 106 is installed for use in step 1112.

The alternative to steps 1110 and 1112 occurs when the use of library 106 has exited the solution space of library 106. As compared to trending out, changes of this type are more severe and are not generally addressable by evolution program 108. In cases of this type, the use of the library is halted and the modeling tool is used to generate results in real time to match the empirical readings measured during the production process (step 1114). This allows production to continue while a new library 106 is created.

Each time a new library is evolved, its production is evaluated. If it is found to be unstable, it may be replaced with the previous library and the evolution process restarted. This provides a fault tolerant approach to library evolution. This sort of fault tolerant operation naturally involves comparing the performance of a newly generated library with the previously used version of the same library. In order to avoid anomalous results during this comparison, it is generally useful to require that the evolution of the new library be completed to a sufficient degree before comparison is made. For example, implementations might require that new versions include a fixed percentage of new predicted measurements before comparison is made. This avoids the situation where an evolved, but highly similar library is actually worse at solving a given set of problems.

Concurrent Library Evolution

The division of tasks between evolution program 108 and the remainder of the components of metrology system 100 means that the evolution process may continue, even as metrology system 100 remains in use. To support concurrent evolution, evolution program 108 may be configured to operate on selected portions of library 106. Evolution program 108 optimizes each selected portion as metrology system 100 continues to use the original version of library 106. When the optimization of a selected portion is complete, evolution program inserts it into library 106. This may be performed using a fault tolerant transaction allowing the optimization to be undone if it turns out to be undesirable in practice.

Alternate Applications

The previous description has focused on the use of library evolution within the context of optical metrology. The use of library evolution is well suited to this context because of the extreme difficulty associated with creating optimal libraries for optical metrology processes. In general, it should be appreciated that these same difficulties may be encountered whenever a library having finite resolution and range is used to characterize an infinite solution space. As a result, the library evolution method described above has general applicability to solve a wide range of different problems. Genomic mapping is one case where a library of solutions may be used to analyze empirical results. Since the possible solution is vast, construction of an optimal library is difficult. Evolving an existing library to match its usage pattern presents a more practical and efficient approach.

It should be recognized that a number of variations of the above-identified embodiments will be obvious to one of ordinary skill in the art in view of the foregoing description. Accordingly, the invention is not to be limited by those specific embodiments and methods of the present invention shown and described herein. Rather, the scope of the invention is to be defined by the following claims and their equivalents.

What is claimed is:

1. An optical metrology system that comprises:
    a plurality of separate optical metrology tools;
    a shared library connected to said metrology tools and including a series of predicted measurement sets, each predicted measurement set corresponding to the empirical measurement sets that the metrology tools would record for a variation of a physical structure;
    an analysis program configured to search the shared library to locate predicted measurement sets that match the empirical measurement sets gathered by the metrology tools, the analysis program also configured to generate a usage pattern for the shared library, the usage pattern identifying the most common searches performed on the shared library; and
    a library evolution tool configured to add one or more new predicted measurement sets to the library to increase the number of predicted measurement sets within the shared library to correspond with the usage pattern so that upon a subsequent search of the library the likelihood of locating a predicted measurement set that better matches an empirically obtained measurement set is increased.

2. An optical metrology system as recited in claim 1 that further comprises a local library associated with one of the optical metrology tools, the local library supplementing the shared library by including the predicted measurement sets most used by the associated optical metrology tool.

3. An optical metrology system as recited in claim 2, wherein the library evolution tool is further configured to reconfigure the local library to correspond with a usage pattern for the local library.

4. A method of analyzing samples with a network including a first optical metrology tool and a second, separate optical metrology tool, the method comprising the steps of:
    generating a first local library associated with the first metrology tool and a second, separate local library associated with the second metrology tool, each library including a series of predicted measurement sets, each predicted measurement set corresponding to the empirical measurement sets that the associated metrology tool would record for a variation of a physical structure;
    independently evolving both the first and second local libraries based on the respective usage of the first and second metrology tools;
    searching the first local library to locate predicted measurement sets that match empirical measurement sets gathered by the first metrology tool; and
    reconfiguring the first metrology tool to use the second local library if the second local library includes predicted measurements sets more closely matching the empirical measurement sets gathered by the first metrology tool.

* * * * *